United States Patent
Roth

(10) Patent No.: US 8,059,003 B2
(45) Date of Patent: Nov. 15, 2011

(54) METHODS FOR PROVIDING SECURE AND TRANSPARENT CACHED IGNITION INTERLOCK DATA

(75) Inventor: Michael D Roth, Scottsdale, AZ (US)

(73) Assignee: Safe Harbor, LLC, Scottsdale, AZ (US)

( * ) Notice: Subject to any disclaimer, the term of this patent is extended or adjusted under 35 U.S.C. 154(b) by 342 days.

(21) Appl. No.: 12/390,995

(22) Filed: Feb. 23, 2009

(65) Prior Publication Data

US 2010/0212986 A1    Aug. 26, 2010

(51) Int. Cl.
*G08B 23/00* (2006.01)

(52) U.S. Cl. .............. 340/576; 340/573.1; 180/272; 600/532

(58) Field of Classification Search .......... 340/576, 340/522, 573.1; 180/272, 279, 287; 280/735; 307/10.1; 600/532; 707/E17.032
See application file for complete search history.

(56) References Cited

U.S. PATENT DOCUMENTS

| | | | |
|---|---|---|---|
| 4,697,666 A | 10/1987 | Collier et al. | |
| 4,912,458 A | 3/1990 | Comeau et al. | |
| 5,224,566 A | 7/1993 | Stepanian et al. | |
| 5,426,415 A | 6/1995 | Prachar et al. | |
| 5,825,283 A | 10/1998 | Camhi | |
| 6,026,674 A | 2/2000 | Gammenthaler | |
| 6,748,792 B1 | 6/2004 | Freund et al. | |
| 6,853,956 B2 | 2/2005 | Ballard, Jr. et al. | |
| 7,204,335 B2 | 4/2007 | Stewart et al. | |
| 7,218,236 B2 | 5/2007 | Mobley et al. | |
| 7,287,617 B2 | 10/2007 | Mobley et al. | |
| 7,299,890 B2 | 11/2007 | Mobley et al. | |
| 7,377,352 B2 | 5/2008 | Mobley et al. | |
| 7,422,723 B1 | 9/2008 | Betsill | |
| 2006/0202842 A1* | 9/2006 | Sofer | 340/576 |
| 2007/0144812 A1 | 6/2007 | Stewart et al. | |
| 2007/0239331 A1 | 10/2007 | Kaplan | |
| 2007/0273537 A1* | 11/2007 | Crespo et al. | 340/576 |
| 2008/0097551 A1 | 4/2008 | Dicks et al. | |

* cited by examiner

*Primary Examiner* — Anh V La
(74) *Attorney, Agent, or Firm* — The Noblitt Group, PLLC

(57) ABSTRACT

Generally, in accordance with various exemplary embodiments of the present invention, the present method comprises collecting data from breath alcohol ignition interlock devices ("BIID" or "IID"), uploading the data from an IID to a central database, pairing the data with secure transactional data to provide one or more secure transactional stamp(s), storing the data and the paired secure transactional stamp(s) in said central database, producing a report comprising said data and the paired transactional stamp, and providing the report to an authorized third party. Preferably, the transactional stamp comprising the name of personnel, time, and any changes made to the data collected from the IID is generated and attached to the data. Further, the present invention discloses methods for transactional stamping all reviews of the IID data and/or all client input data to produce a secure report, admissible under the Federal Rules of Evidence.

25 Claims, 4 Drawing Sheets

METHODS FOR PROVIDING SECURE AND TRANSPARENT CACHED IGNITION INTERLOCK DATA

FIELD OF INVENTION

The present invention relates generally to a method for providing secure and transparent cached ignition interlock data from a breath alcohol ignition interlock devices ("BIID" or "IID"). Generally, as illustrated in FIG. 1 and in accordance with various exemplary embodiments of the present invention, the present method comprises interfacing a central database with an IID, uploading data from an IID to a central database, pairing said data with secured transactional data to provide one or more secure transactional stamp(s), storing said data and said paired secure transactional stamp(s) in said central database, producing a report with said data and said paired transactional stamp, and providing said report to an authorized third party.

Preferably, the collection of data from the IID is completed at a remote location, is then uploaded to a central database, and contemporaneously stamped. Most preferably, in accordance with the various exemplary embodiments of the present invention, contemporaneous with the uploading of the data collected from the IID a transactional stamp comprising the name of personnel, time, and any changes made to the data collected from the IID is generated and attached to the data.

Further, in accordance with the various exemplary embodiments of the present invention, the present invention discloses methods for transactional stamping reviews of the IID data by personnel and/or transactional stamping client input data. Additionally, in accordance with the various exemplary embodiments of the present invention, a secure report, admissible under the Federal Rules of Evidence comprising at least one of the following: the data collected from the IID; blood alcohol concentration ("BAC") violations; hardware/software failures; personnel review data; client input data; and all corresponding transactional stamps may be provided to the motor vehicle department ("MVD"), government, and/or any authorized third party.

BACKGROUND OF THE INVENTION

Vehicle operation by persons under the influence of alcohol is a well known safety hazard in the United States and throughout the world. Thousands of deaths per year in the United States are attributable to drivers operating vehicles under the influence of alcohol. To address this problem, the state of Arizona, like most states, has established laws that criminalize operation of a vehicle and other machinery with a blood alcohol concentration ("BAC") greater than a preset value (e.g., 0.08% BAC).

To reduce the rate of recidivism of driving under the influence, the state of Arizona and other states require the installation of devices in the vehicles and other machinery of individuals convicted of driving under the influence of alcohol. Such devices, which are commonly referred to as breath alcohol ignition interlock devices ("BIID" or "IID") and/or systems. These BIIDs have been developed to be directly connected to a vehicle's ignition system and are designed to prevent automobiles and other machinery from being operated by inebriated individuals.

IIDs may comprise semiconductor sensors, commonly referred to as a Taguchi cell, infrared absorption sensing systems, and/or fuel cells to sense and quantify the amount of alcohol in a driver's breath. Most modern IIDs use an ethanol-specific fuel cell for a sensor. See U.S. Pat. No. 4,487,055, U.S. Pat. No. 6,026,674, U.S. Pat. No. 6,167,746, and/or U.S. Pat. No. 7,204,335. A fuel cell sensor is an electrochemical device in which alcohol undergoes a chemical oxidation reaction at a catalytic electrode surface (platinum) to generate an electric current. This current is then measured and converted to an alcohol equivalent reading. Although fuel cell technology is not as accurate or reliable as infrared spectroscopy technology used in evidentiary breathalyzers, they are less expensive and specifically tailored to quantify ethyl alcohol (drinking alcohol). Among manufacturers of IIDs are Smart Start Inc., LifeSafer Interlock, SOS, Ignition Interlock Systems, Intoxalock and Monitech. A list of federally-approved IID devices is maintained by the National Highway Traffic Safety Administration ("NHTSA") in its NHTSA Conforming Products List.

Typically, in order to start a vehicle equipped with an IID, the driver must first blow into the breath analyzer installed in the vehicle or machinery. Conventional IIDs measure the alcohol content of the breath and calculate BAC readings on the alcohol content of gas present in the alveoli of the lungs by approximating, through the use of software algorithms, the alcohol content in the bloodstream. If the driver's BAC exceeds a preset limit, the vehicle's ignition is disabled and the vehicle is rendered inoperable. If the driver's BAC is below the preset limit, ignition is permitted and the vehicle may be started. Exemplary ignition interlock devices that utilize breath analyzers are described in, for example, U.S. Pat. Nos. 3,780,311, 3,824,537, 3,831,707, 4,592,443, and 4,697,666.

Unfortunately, individuals required to use IIDs have become increasingly sophisticated in attempting to trick the device to register false negatives and, in turn, to allow them to drive intoxicated. For example, individuals have been known to have a sober passenger blow into the device and/or use bogus gas samples from balloons or bicycle pumps. Accordingly, the IIDs have become increasingly sophisticated in ensuring that the person providing a breath sample is the person operating the vehicle or machinery. Routinely, IIDs will require a negative pressure (sucking), a positive pressure (blowing), a series of blowing and/or sucking by the operator, and/or retesting while operating the equipment or vehicle. Another deterrent is the Random Rolling Retest. These are random times when the operator is required to provide additional breath samples. This prevents Drinking while driving. Another reason for this is to ensure that an individual cannot have another person provide the first sample to get the car started and then drive home without that person. Most Manufactures set them from within the first 5 to 15 minutes then every 30 to 60 minutes.

Similarly, some of the more onerous IIDs require secondary testing and verification of identity by the operator. For example, along with a breath sample analysis, U.S. Pat. No. 4,158,198 discloses an IID, which incorporates an evaluation of the actual driving by way of a "steady control task" for a designated period of time; U.S. Pat. No. 4,645,939 discloses an IID, which incorporates an evaluation of reflexes using a sequence of time intervals; U.S. Pat. No. 4,723,625 discloses an IID, which incorporates an evaluation of reflexes using a series of test buttons; U.S. Pat. No. 4,738,333 discloses an IID, which incorporates an evaluation of physical tasks, to confirm identity of the driver; and U.S. Pat. No. 6,748,792 and/or United States Patent Publication No. 20070144812 discloses IIDs, which incorporate video cameras to photograph the person giving a breath sample.

Generally, the methods for detecting BAC and using ignition interlock systems to prevent automobiles and other machinery, from being operated by inebriated individuals are well known in the current art. Moreover, the current invention does not rely on any particular ignition interlock device or method for testing BAC, but instead can be universally applied to any ignition interlock data retrieved from any ignition interlock device installed on any vehicle or equipment.

While the internal hardware and the function of these IIDs are well known in the art, the software used to run, maintain, and report BAC results to the courts and government agencies is not well known. This is due to the fact that the software is typically maintained under trade secret either by the manufacturers of the IID or the companies that service the IIDs. To solve this lack of transparency into the software algorithms and computation, the National Highway Traffic Safety Administration (NHTSA) developed model specifications for breath alcohol IIDs, which were passed into federal law in 1992, as published in the Federal Register, Vol. 57, No. 67, Apr. 7, 1992, pp. 11774-11787. These NHTSA standards for IIDs have been adopted by most states including, but not limited to Arizona.

While these NHTSA standards for IIDs require that the IIDs operate within certain engineering tolerances, they do not require reporting of false positives, false negatives, device failures, and/or maintenance logs for the installed IID. Accordingly, there is no way for the court, MVD, or any other authorized third party to investigate the operating history of an IID and to validate the reliability of the BAC readings. Currently, the IIDs and the IID software algorithms lack transparency and do not allow for an authorized third party to verify and validate tests results.

We estimate that most common IIDs have a rate of failure of between 35 to 6% depending on the manufacture, and maintenance, and that these hardware failures are currently either being disregarded or being reported as a false positive or false negative. Thus, a method for providing a secured and transparent cached ignition interlock data from an IID showing a history of IID operation is needed and is provided herein. The penalties for BAC violations recorded by a client's IID range from monetary fines to Probation violations and prison. Clients have a real and vested interest in the accuracy and refutability of recorded violations. Because of the nature of the breath testing methodology the requirement of Random Rolling Retest causes false violations. The "Partition ration" or formula used to equate ones Breath alcohol lever with ones Blood alcohol level is to multiply the alcohol reading by 2400. That is to say multiply the reading two thousand four hundred times to achieve the blood equivalent. Because of this Breath alcohol is a significant problem. Evidentiary machines used to test BRAC require a 15 minute depravation period where the law enforcement officer is required to swear that the defendant at no time prior to the breath test burped, or regurgitated anything in their mouth, as to produce mouth alcohol and provide an invalid breath test. Many drivers eat and or drink as they are driving. Many products that do not contain as their primary ingredients may contain alcohol. Many other item produce alcohol as a byproduct as they decay or heat. An Example is that Smoothies that are available in the retail environment utilize over ripe bananas because of their high fructose levels. A known bi-product of the Fruit Ripening process is alcohol. This small amount of alcohol when multiplied by the patrician ration causes false violation. Under most current systems this leaves two options. The violation gets reported to the authorities and the defendant must try to remember what may have caused the violation. The technician who uploads the data from the handset may review the log with the individual and alter or "correct" the log and the violation real or unreal will not be reported. The second option destroys the integrity of the data and evidence as it destroys the evidence chain.

Additionally, the NHTSA standards do not require reporting of time, date, and place of detected BAC violations, nor do the NHTSA standards require that personnel responsible for monitoring the IID hard ware and software report the time, date, or place of any changes made to the IID data prior to reporting to the court, MVD or other authorized third party. Due to the lack of reporting requirements under the NHTSA standards, criminal courts have exhibited reluctance in certain cases to admit evidence excusing a reported BAC violation and/or admitting evidence of false positive test results. Thus, a method for providing a secured and transparent cached ignition interlock data from an IID, review of the IID data by IID personnel, and storing client input data to evidence a credible chain of evidentiary custody is needed and is provided herein.

SUMMARY OF THE INVENTION

The present invention relates generally to a method for providing secure and transparent cached ignition interlock data from a breath alcohol ignition interlock devices ("BIID" or "IID"). Generally, as illustrated in FIG. 1 and in accordance with various exemplary embodiments of the present invention, the present method comprises interfacing a central database with an IID, uploading data from an IID to a central database, pairing said data with secured transactional data to provide one or more secure transactional stamp(s), storing said data and said paired secure transactional stamp(s) in said central database, producing a report with said data and said paired transactional stamp, and providing said report to an authorized third party.

Preferably, the collection of data from the IID is completed at a remote location, is then uploaded to a central database, and contemporaneously stamped. Most preferably, in accordance with the various exemplary embodiments of the present invention, contemporaneous with the uploading of the data collected from the IID a transactional stamp comprising the name of personnel, time, and any changes made to the data collected from the IID is generated and attached to the data.

Further, in accordance with the various exemplary embodiments of the present invention, the present invention discloses methods for transactional stamping reviews of the IID data by personnel and/or transactional stamping client input data. Additionally, in accordance with the various exemplary embodiments of the present invention, a secure report, admissible under the Federal Rules of Evidence comprising at least one of the following: the data collected from the IID; blood alcohol concentration ("BAC") violations; hardware/software failures; personnel review data; client input data; and all corresponding transactional stamps may be provided to the motor vehicle department ("MVD"), government, and/or any authorized third party.

BRIEF DESCRIPTION OF THE DRAWING

A more complete understanding of the present invention, however, may best be obtained by referring to the detailed description when considered in connection with the drawing figures, wherein like numerals denote like elements and wherein.

DETAILED DESCRIPTION OF EXEMPLARY EMBODIMENTS

The detailed description of exemplary embodiments of the invention herein shows various exemplar embodiments and the best modes known to the inventors at this time. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those of reasonable skill in the art. Additionally, all included figures are non-limiting illustrations of the exemplary embodiments and modes, which similarly avail themselves to any equivalent modes or embodiments that are known or obvious to those of reasonable skill in the art.

Figure 1:
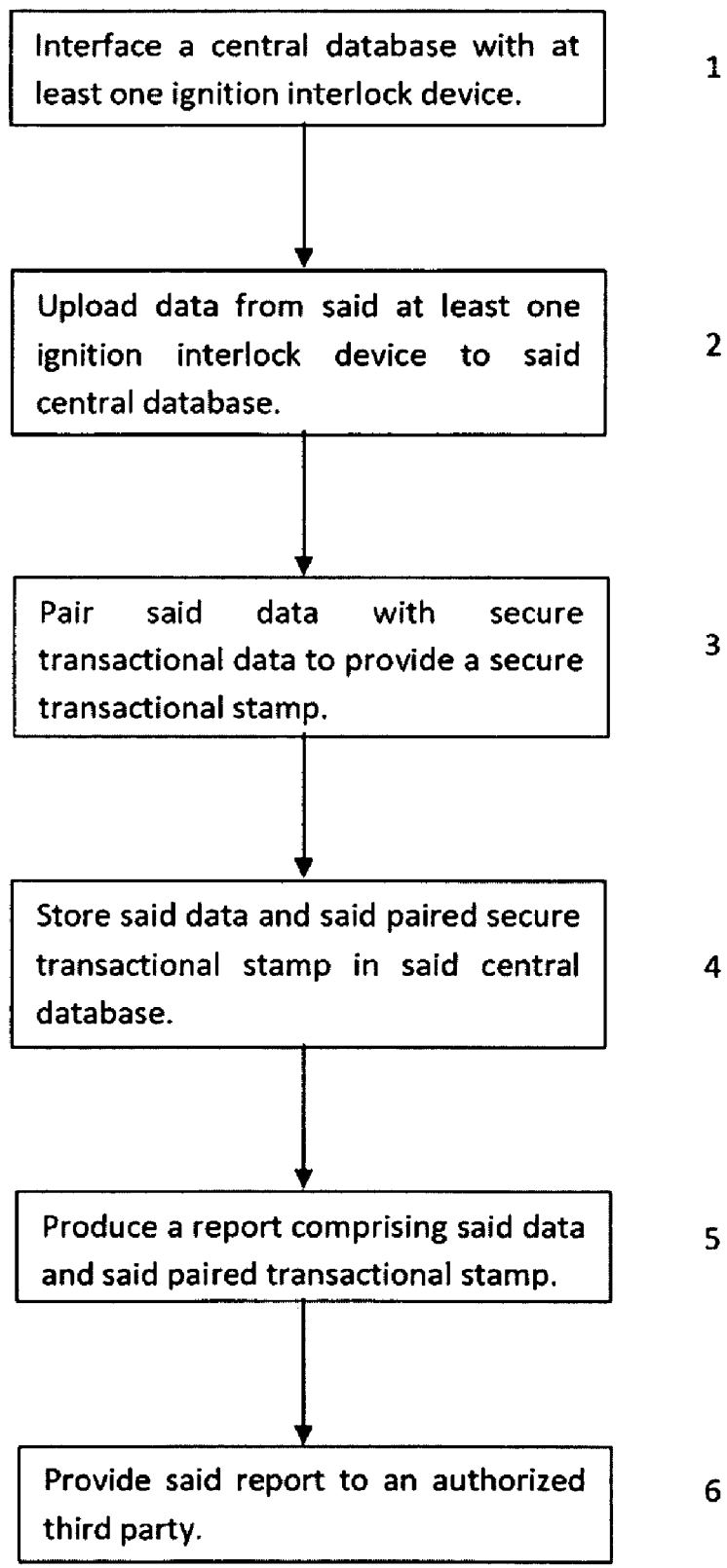
FIG. 1 illustrates a general method for providing secured and transparent cached ignition interlock data from a breath alcohol ignition interlock devices ("BIID" or "IID") in accordance with one exemplary embodiment of the present invention.

The present invention relates generally to a method for providing secured and transparent cached ignition interlock data from a breath alcohol ignition interlock devices ("BIID" or "IID"). Generally, as illustrated in FIG. 1 and in accordance with the various exemplary embodiments of the present invention, the present method comprises interfacing a central database with an IID 1, uploading data from an IID to a central database 2; pairing said data with secured transactional data to provide a secure transactional stamp 3, storing said data and said paired secure transactional stamp in said central database 4, producing a report with said data and said paired transactional stamp 5, and providing said report to an authorized third party 6.

In accordance another exemplary embodiment of the present invention, IIDs may comprise semiconductor sensors, commonly referred to as a Taguchi cell, infrared absorption sensing systems, and/or fuel cells to sense and quantify the amount of alcohol in a driver's breath. Most modern IIDs use an ethanol-specific fuel cell for a sensor. See U.S. Pat. No. 4,487,055, U.S. Pat. No. 6,026,674, U.S. Pat. No. 6,167,746, and/or U.S. Pat. No. 7,204,335. A fuel cell sensor is an electrochemical device in which alcohol undergoes a chemical oxidation reaction at a catalytic electrode surface (platinum) to generate an electric current. This current is then measured and converted to an alcohol equivalent reading. Although fuel cell technology is not as accurate or reliable as infrared spectroscopy technology used in evidential breathalyzers, they are less expensive and specifically tailored to quantify, ethyl alcohol (drinking alcohol). Among manufacturers of IIDs are Draeger Interlock (selling the Draeger Interlock® XT. See www.azsafeharbor.net), Smart Start Inc. (www.smartstartinc.com), LifeSafer Interlock (http://www.lifesafer-.com), SOS, Ignition Interlock Systems (See www.aziid-.com), Consumer Safet, Technology, Inc. (Selling the Intoxalock. See www.arizmat.com), Alcohol Detections Systems, Inc. (Selling The Determinator®. See www.stopdwi-.com), Guardian Interlock (Selling the AMS 2000. See www-.guardianinterlockaz.com), and Monitech (Selling the QuicTest. See http://www.monitechnc.com/QuicTest1.html). A list of federally-approved IID devices is maintained by the National Highway Traffic Safety, Administration ("NHTSA") in its NHTSA Conforming Products List.

One of reasonable skill in the art understands that many new devices are currently being developed and may be developed in the future for sensing, detecting, and quantifying BAC and drug analytes in an individual including sweat sensors and/or percutaneous light sensors. By way of non-limiting example, an IID may include a transdermal BAC reader as disclosed in U.S. Pat. No. 7,413,047 and/or a non-invasive BAC reader and IID as disclosed in U.S. Pat. No. 5,743,349. One of reasonable skill in the art will understand that all of this numerous devices for sensing, detecting, and quantifying BAC and drug analytes are contemplated and disclosed herein.

Generally, the methods for detecting BAC and using ignition interlock systems to prevent automobiles and other machinery from being operated by inebriated individuals are well known in the current art. Moreover, the current invention does not rely on any particular ignition interlock device or method for testing BAC or drug analytes, but instead can be universally applied to any ignition interlock data retrieved from any ignition interlock device installed on any equipment.

As illustrated in FIG. 1 and in accordance with the various exemplary embodiments of the present invention, the central database may be interfaced with any number of IIDs 1 via one or more wireless connections and/or one or more wired connections. In accordance with the various exemplary embodiments of the present invention, the central database is interfaced with any number of IIDs 1 via a wired connection comprising at least one of a USB connection, an Ethernet connection, a DIN connection, a DVI connection, a VGA connection, a DB13W3 connection, and a D-Terminal connection.

Alternatively, as illustrated in FIG. 1 and in accordance with the various exemplary embodiments of the present invention, the central database may, be interfaced with any number of IIDs 1 via one or more wireless connections comprising at least one of a wireless access network connection.

As illustrated in FIG. 1 and in accordance with the various exemplary embodiments of the present invention, after interfacing one or more central database(s) with any number of IIDs via any means known to a person of reasonable skill in the art, data is uploaded from the IID(s) to the central database 2. In accordance with the various exemplary embodiments of the present invention, the data collected from the IID(s) may comprise blood alcohol concentration (BAC) or drug analyte test results, diagnostic information of said at least one ignition interlock device, warnings of hardware failures of said at least one ignition interlock device, speed of vehicle, GPS position, or other information contained in the "Black Box" blinker on or off braking etc. or information concerning the verification of the operator's identity.

As illustrated in FIG. 1 and in accordance with the various exemplary embodiments of the present invention, after uploading data from any number of IIDs to one or more central database(s), the data is paired with secured transactional data to provide a secure transactional stamp 3. In accordance with the various exemplary embodiments of the present invention, the secured transactional data may comprise at least one of a time data denoting the time at which said data was collected, a date data denoting the date at which said data was collected, an operator data denoting the name of the operator who uploaded said data from said at least one ignition interlock device, and a programming data describing any programming changes to said data uploaded from said at least one ignition interlock device.

In accordance with the various exemplary embodiments of the present invention, the secure transactional stamp may comprise at least one of a time stamp denoting the time at which said data was collected, a date stamp denoting the date at which said data was collected, an operator stamp denoting the name of the operator who uploaded said data from said at least one ignition interlock device, and a programming stamp describing any programming changes to said data uploaded from said at least one ignition interlock device.

As illustrated in FIG. 1 and in accordance with the various exemplary embodiments of the present invention, after creating a secure transactional stamp by pairing the data from one or more IIDs with the secured transactional data, both the data and the paired secure transactional stamp in are stored in the central database 4. In accordance with the various exemplary embodiments of the present invention, the data and the paired secure transactional stamp in are stored in the central database and are subject to security protocols to ensure chain of custody of the information and to foreclose tampering with either the IID data or the paired secure transactional stamp. In accordance with the various exemplary embodiments of the present invention, the central database may comprise a secured computer server.

As illustrated in FIG. 1 and in accordance with the various exemplary embodiments of the present invention, after storing both the data and the secure transactional stamp, a secure report may be produced that catalogues both the data and any paired secure transactional stamp 5. In accordance with the various exemplary embodiments of the present invention, the secure report may be compiled in any formatting and in any manner suitable to show both the IID data and the corresponding secure transactional stamp.

In accordance with the various exemplary embodiments of the present invention, the secure report evidences an evidentiary chain of custody in authenticating evidence as required under the Federal Rules of Evidence including, but not limited to Rule 901(a) and Rule 901(b), namely, Rule 901(b)(9). Similarly, in accordance with the various exemplary embodiments of the present invention, the secure report evidences an evidentiary chain of custody that is a self-authenticating record kept in the customary course of business under the Federal Rules of Evidence including, but not limited to Rule 803(6), Rule 902, namely, Rule 902(11).

Further, in accordance with the various exemplary embodiments of the present invention, the secure report may be compiled in any formatting and in any manner suitably configured to ensure chain of custody of the information and to foreclose tampering with either the IID data or the paired secure transactional stamp. One of reasonable skill in the art understands that numerous formats including, but not limited to, spreadsheets, are contemplated and disclosed herein.

As illustrated in FIG. 1 and in accordance with the various embodiments of the present invention, after a secure report comprising both the data and the secure transactional stamp is produced, the secure report may be provided to an authorized third party 5. In accordance with the various exemplary embodiments of the present invention, an authorized third party may comprise at least one of a member of court personnel, a member of motor vehicle department personnel, and a member of police department personnel. Further, in accordance with the various exemplary embodiments of the present invention, an authorized third party may comprise any court or administrative personnel in the State of Arizona.

Figure 2:
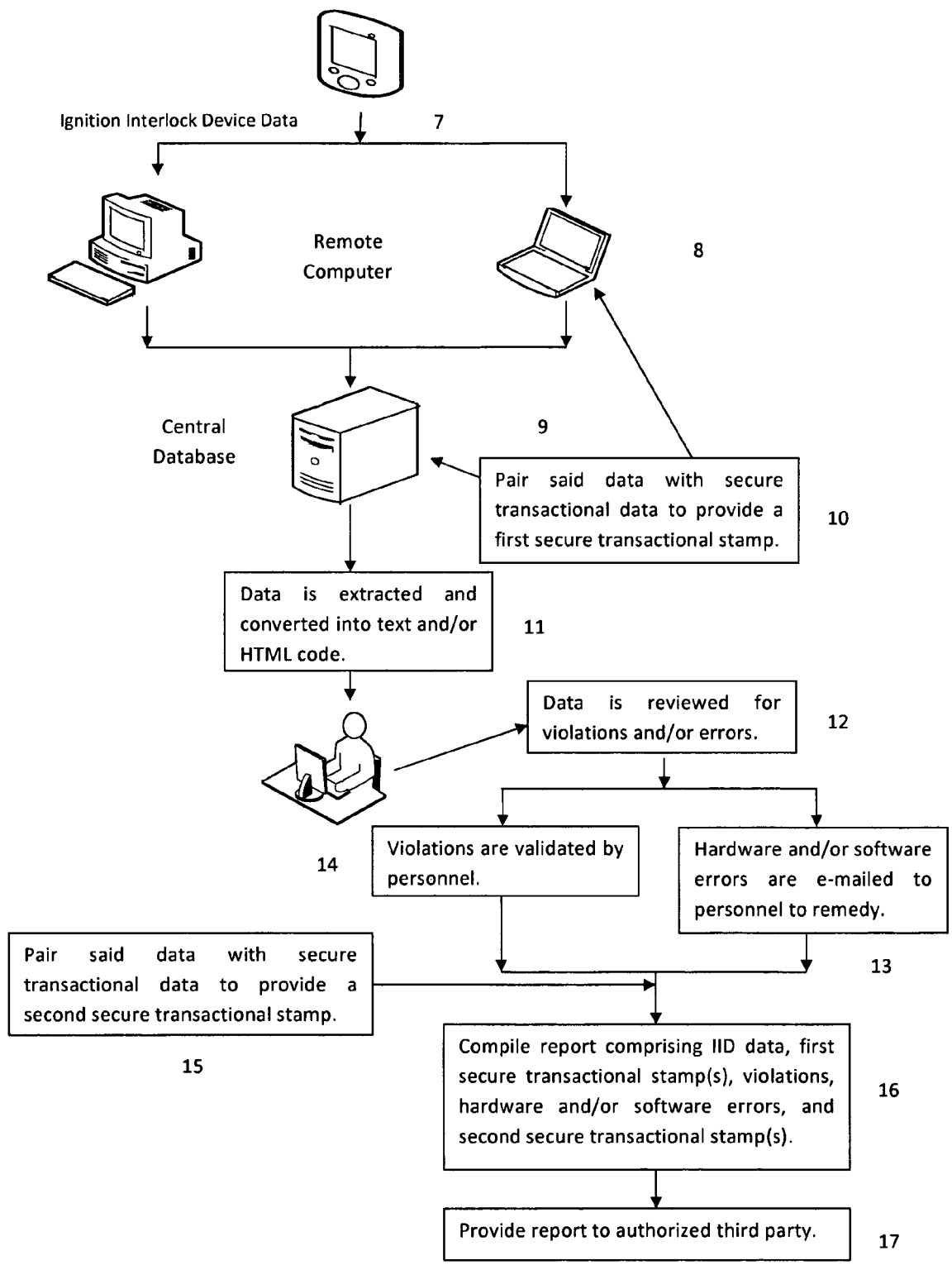
FIG. 2 illustrates a detailed schematic of a method for reporting secured and transparent cached ignition interlock data from a breath alcohol ignition interlock devices ("BIID" or "IID") in accordance with an exemplary embodiment of the present invention.

Generally, as illustrated in FIG. 2, in accordance with the various exemplary embodiments of the present invention, data is uploaded from one or more IIDs 7 to a remote computer 8. As illustrated in FIG. 2, in accordance with the various embodiments of the present invention, the present method comprises interfacing an IID with one or more remote computer(s) 8. In accordance with the various exemplary, embodiments of the present invention, interfacing one or more remote computer(s) 8 with any number of IIDs by any means discussed above and/or any means known to a person of reasonable skill in the art is contemplated and disclosed herein.

Preferably, in accordance with the various exemplary embodiments of the present invention, the remote or local computer(s) 8 may comprise at least one of a personal digital assistant (PDA) computer, a laptop computer, and a desktop computer. In accordance with the various exemplary embodiments of the present invention, the remote computer(s) 8 may comprise any remote or local electronic storage media know by one of reasonable skill in the art suitable for storing and transferring data.

In accordance with the various exemplary embodiments of the present invention, using any type, model, or architecture of the IID(s) discussed above and/or any type, model, or architecture of the IID(s) known to a person of reasonable skill in the art is contemplated and disclosed herein.

Similarly, as illustrated in FIG. 2, in accordance with the various exemplary embodiments of the present invention, any type and sampling rate of the data uploaded from the IID(s) 7 to a remote computer 8 discussed above and/or any typical output data for IIDs as known by one of reasonable skill in the art is contemplated and disclosed herein.

As illustrated in FIG. 2, after the IID is interfaced with the remote computer(s) 8 and the IID data 7 is uploaded, the IID data 7 may be paired with secured transactional data to provide a first secure transactional stamp 10. In accordance with the various exemplary embodiments of the present invention, any secured transactional data 10 paired with the uploaded IID data 7 discussed above and/or any secured transactional data 10 known by one of reasonable skill in the art is contemplated and disclosed herein.

As illustrated in FIG. 2, in accordance with the various exemplary embodiments of the present invention, the IID data 7 and the first secured transactional stamp 10 comprising the paired transactional stamp data may be transmitted from a remote or local computer(s) 8 to a central database 9. FIG. 2 shows that the IID data 7 and the first secured transactional stamp 10 comprising the paired transactional stamp data may be stored and processed in the central database 9. In accordance with the various exemplary embodiments of the present invention, the IID data 7 and the first secured transactional stamp 10 may be processed in to text and/or html computer code 11. One of reasonable skill in the art will understand that numerous types of computer processing and potential data formats are contemplated and disclosed herein.

As discussed above, in accordance with the various exemplary embodiments of the present invention, after appropriate processing of the IID data 7 and the first secured transactional stamp 10 may be reviewed for BAC violations and software/hardware errors 12. As illustrated in FIG. 2, in accordance with the various exemplary embodiments of the present invention, during the review 12 BAC violations are validated 14 and software and/or hardware errors are e-mailed to service personnel to correct 13. At the conclusion of the review of the IID data 7 and the first secured transactional stamp 10, in accordance with the various exemplary embodiments of the present invention, service personnel's interaction during the review of the IID data 7 and the first secured transactional stamp 10 may be logged and paired with a second set of secured transactional data 15. One of reasonable skill in the art will understand that processing of IID data, reviewing IID data, and transactional stamping of IID data and review data at the remote or local computer is contemplated and disclosed herein, but the most efficient method of processing, reviewing, and securing transactional data is to complete all functions in a central database/computer.

In accordance with the various exemplary embodiments of the present invention, his second set of secured transactional data 15, as with the first set of secured transactional data may comprise at least one of a time data denoting the time at which the review was conducted, a date data denoting the date at which the review was conducted, an operator data denoting the name of the operator who conducted the review, and a programming data describing any programming changes during the review.

As illustrated in FIG. 2, in accordance with the various exemplary embodiments of the present invention, the second set of secured transactional data 15 creates a second transaction stamp. In accordance with the various exemplary embodiments of the present invention, this second transaction stamp comprising a second set of secured transactional data 15, along with any additional transaction stamps, may be stored in either the remote or local computers and/or the central database. One of reasonable skill in the art will understand that numerous sets of reviews may be conducted with numerous paired secured transactional data creating numerous secure transaction stamps. Additionally, one of reasonable skill in the art will understand that the present invention discloses a method to securely log and cache all IID data input into the remote or local computers and/or the central database and to securely log and cache all reviews and/or alterations of the IID data within the remote or local computers and/or the central database.

As discussed above, in accordance with the various exemplary embodiments of the present invention, multiple, secure transactional stamps preserve IID data creating a credible chain of evidentiary custody is needed and is provided herein. Reliable and validated transparency in recordation of violations, information modification, access by personnel, and client notations constructs a sound basis for the creation of a credible chain of evidentiary custody.

As illustrated in FIG. 2, in accordance with the various exemplary embodiments of the present invention, after all that processing of IID data, reviewing IID data, and transactional stamping of IID data and review data, a secure report may be created comprising at least one of the IID data, the first secure transactional stamp, BAC violations, hardware and/or software errors, the second (and any subsequent) transactional stamp(s) 16. Further, the secure report may be provided to an authorized third party. As discussed above, in accordance with the various exemplary embodiments of the present invention, the authorized third party may comprise any party with requisite authorization to view the report including, but not limited to, a member of court personnel, a member of motor vehicle department personnel, and/or a member of police department personnel in the State of Arizona.

Figure 3:
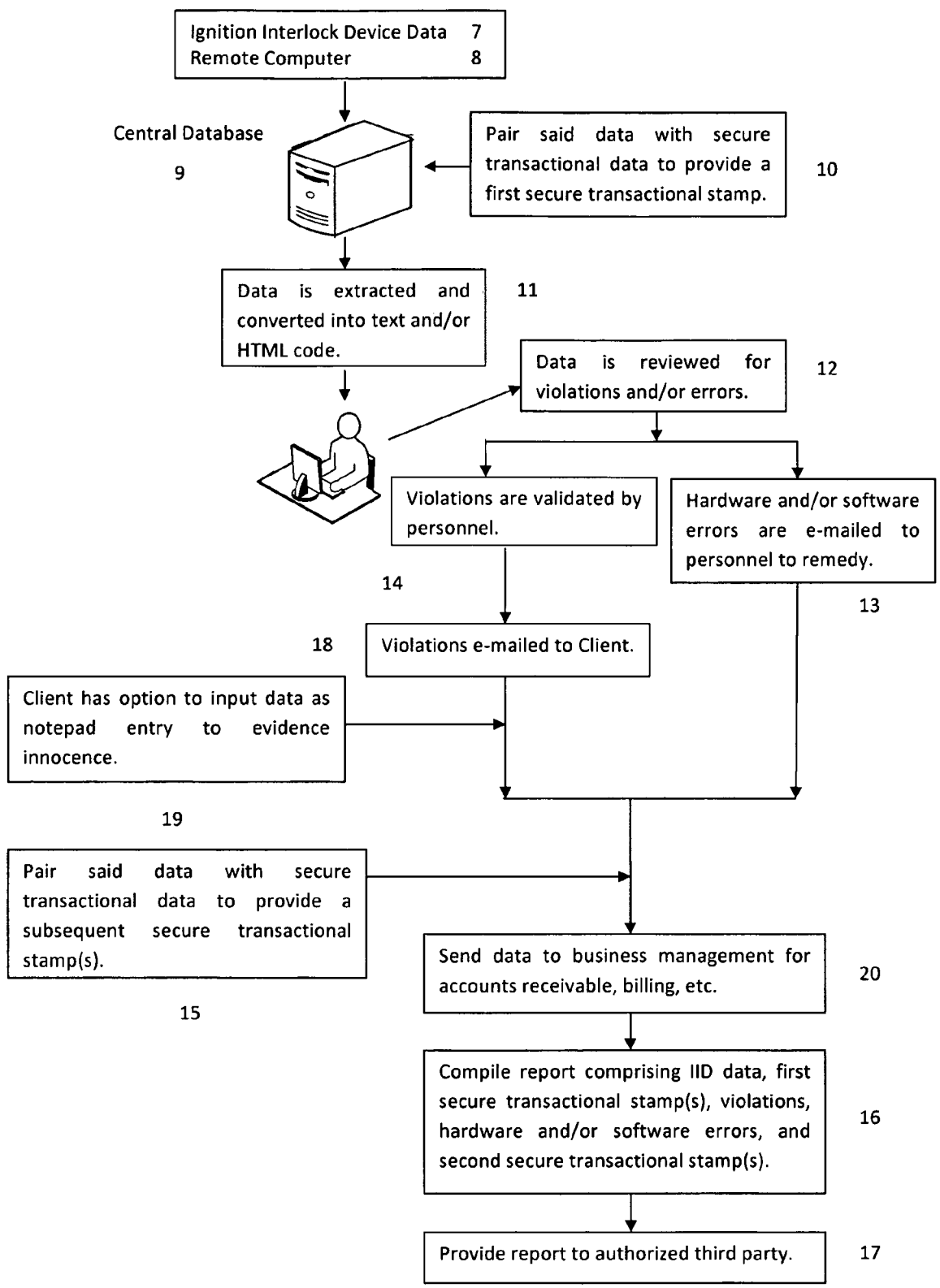
FIG. 3 illustrates a detailed schematic of a method for logging client commentary and business data in connection with secured and transparent cached ignition interlock data from a breath alcohol ignition interlock devices ("BIID" or "IID") in accordance with an exemplary embodiment of the present invention.

Additionally, in accordance with the various exemplary embodiments of the present invention, FIG. 3 illustrates a detailed schematic of a method for logging client commentary in connection with secured and transparent cached IID data. As illustrated in FIG. 3 and discussed above, in accordance with the various exemplary embodiments of the present invention, during the review 12 BAC violations are validated 14 and, optionally, sent to clients 18. One of reasonable skill in the art will understand that noticing of these violations may be completed via numerous means including, but not limited to, e-mail and/or United States mail and that all of these noticing means are disclosed and contemplated herein.

Further, as illustrated in FIG. 3, in accordance with the various exemplary embodiments of the present invention, after a BAC violations is optionally sent to a client 18, the client may enter data into the system as a notepad entry to evidence innocence 19. For example, if a client with an IID takes his car to a restaurant with a valet service, the valet uses the IID to start the vehicle, and the valet registers a violation, then the client may annotate the notepad to describe the event and/or upload data to corroborate the client's story (i.e. upload a copy of the valet ticket). It is apparent to a skilled criminal defense attorney that this corroborating evidence may increase the credibility of the evidence and the chance of a court disregarding the recorded BAC violation.

Likened to the method shown in FIG. 2, FIG. 3 illustrates an exemplary embodiment of the present invention, wherein the subsequent set of secured transactional data 15, similar to the first set of secured transactional data may comprise at least one of time data denoting the time at which the client entered data, date data denoting the date at which the client entered data, and event data describing any events and/or special circumstances entered by the client.

As illustrated in FIG. 3, in accordance with the various exemplary embodiments of the present invention, the subsequent set of secured transactional data 15 creates a subsequent transaction stamp. In accordance with the various exemplary embodiments of the present invention, this subsequent transaction stamp comprising a subsequent set of secured transactional data 15, along with any additional transaction stamps, may be stored in either the remote or local computers and/or the central database 9. One of reasonable skill in the art will understand that numerous sets of clients' notes and/or data may be stored with numerous paired secured transactional data creating numerous secure transaction stamps. Additionally, one of reasonable skill in the art will understand that the present invention discloses a method to securely log and cache all IID data input into the remote or local computers and/or the central database and to securely log and cache all client input data within the remote or local computers and/or the central database.

Again, as illustrated in FIG. 3, in accordance with the various exemplary embodiments of the present invention, all BAC violations 14, software and/or hardware errors 13, and/or client data input may be sent to business management personnel for accounts receivable, billing, and/or other managerial processing tasks 20.

Figure 4:
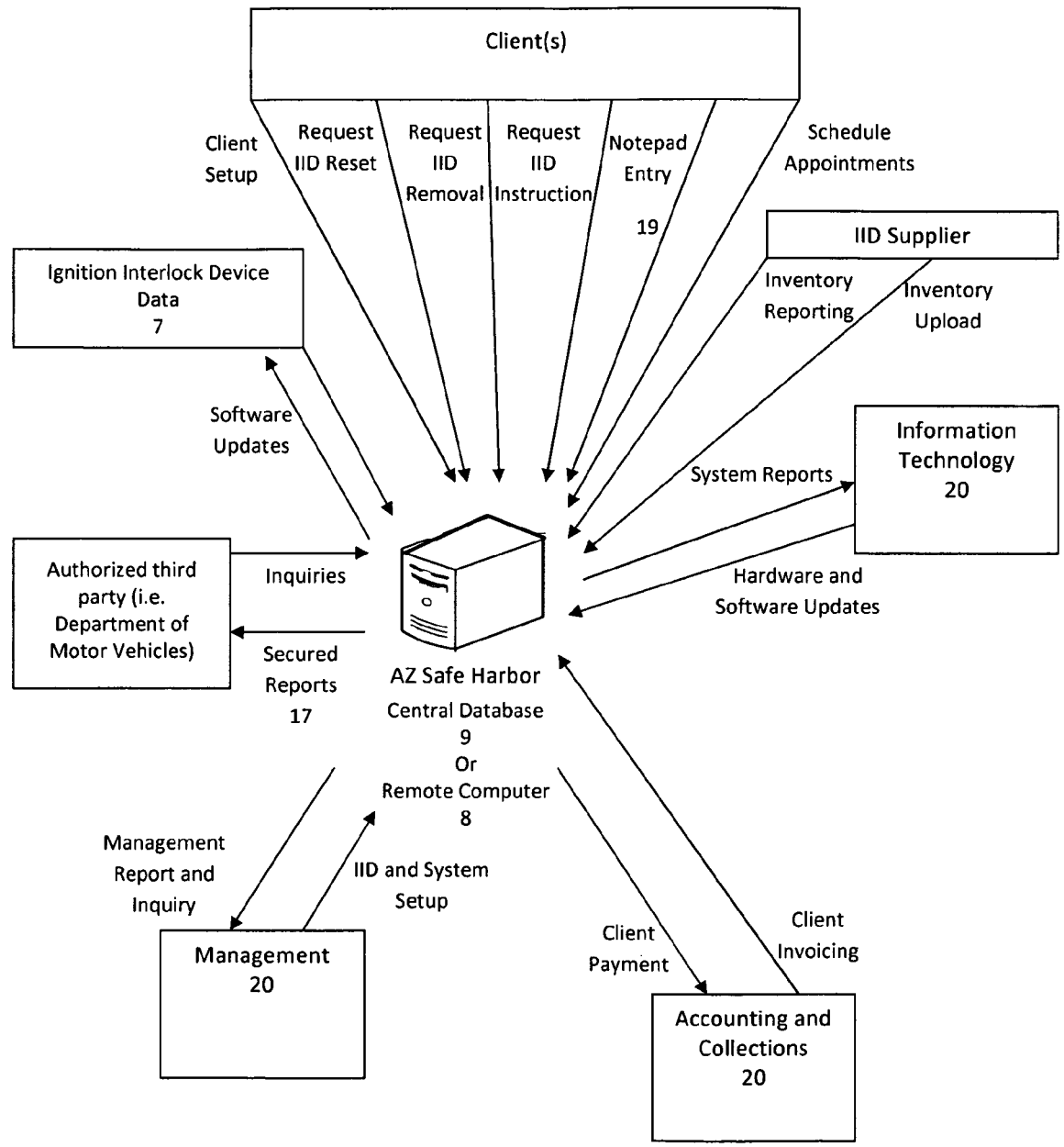
FIG. 4 illustrates a system overview for providing secured and transparent cached ignition interlock data from a breath alcohol ignition interlock devices ("BIID" or "IID") in accordance with an exemplary embodiment of the present invention.

In accordance with the various exemplary embodiments of the present invention, FIG. 4 illustrates a detailed system overview for providing secured and transparent cached IID data. FIG. 4, in accordance with the various exemplary embodiments of the present invention, illustrates all of the interfacing, stamping, storing, processing, reporting, managerial functions, and/or client feedback steps discussed above. Preferably, as shown in FIG. 4, in accordance with the various exemplary embodiments of the present invention, the system is called "Arizona Safe Harbor," "AZ Safe Harbor." and/or "Safe Harbor."

Moreover, unless specifically noted, it is the Applicant's intent that the words and phrases in the specification and the claims be given the commonly accepted generic meaning or an ordinary and accustomed meaning used by those of reasonable skill in the applicable arts. In the instance where these meanings differ, the words and phrases in the specification and the claims should be given the broadest possible, generic meaning. If it is intended to limit or narrow these meanings, specific, descriptive adjectives will be used. Absent the use of these specific adjectives, the words and phrases in the specification and the claims should be given the broadest possible meaning. If any other special meaning is intended for any word or phrase, the specification will clearly state and define the special meaning.

As used herein, the terms "comprise", "comprises", "comprising", "having", "including", "includes", or any variation thereof, are intended to reference a non-exclusive inclusion, such that a process, method, article, composition or apparatus that comprises a list of elements does not include only those elements recited, but can also include other elements not expressly listed and equivalents inherently known or obvious to those of reasonable skill in the art. Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters or other operating requirements without departing from the scope of the instant invention and are intended to be included in this disclosure.

The use of the words "function", "means" or "step" in the specification or claims is not intended to invoke the provisions of 35 USC 112, Paragraph 6, to define the invention. To the contrary, if such provisions are intended to be invoked to define the invention, then the claims will specifically state the phrases "means for" or "step for" and a function. Contrastingly, the intention is NOT to invoke such provision when then claims cite a "means for" or a "step for" performing a function with recitation of any structure, material, or act in support of the function. If such provision is invoked to define the invention it is intended that the invention not be limited only to the specific structure, materials, or acts that are described in the preferred embodiments, but in addition to include any and all structures, materials, or acts that perform the claimed function, along with any and all known or later-developed equivalent materials, structures, or acts for performing the claimed function.

What is claimed is:

1. A method for providing secured and transparent cached ignition interlock data from a breath alcohol ignition interlock device comprising:
    interfacing a central database with at least one ignition interlock device;
    uploading data from said at least one ignition interlock device to said central database;
    pairing said data with secured transactional data to provide a secure transactional stamp;
    storing said data and said paired secure transactional stamp in said central database;
    producing a report with said data and said paired transactional stamp; and
    providing said report to an authorized third party.

2. The method of claim 1, wherein said at least one ignition interlock device comprises at least one of a Taguchi cell, an infrared absorption sensing system, and a fuel cell configured to sense and quantify the amount of alcohol in a client's breath sample.

3. The method of claim 1, wherein said at least one ignition interlock device comprises at least one of a DRAEGER INTERLOCK® XT device, an Intoxalock device, a LifeSafer Interlock device, a Smart Start's ignition interlock device, an AMS 2000 device, a QuicTest device, and The Determinator device.

4. The method of claim 1, wherein said interface between said central database and said at least one ignition interlock device comprises at least one of a wireless connection and a wired connection.

5. The method of claim 4, wherein said wired connection comprises at least one of a USB connection, an Ethernet connection, a DIN connection, a DVI connection, a VGA connection, a DB13W3 connection, and a D-Terminal connection.

6. The method of claim 4, wherein said wireless connection comprises at least one of a wireless access network connection.

7. The method of claim 1, wherein said data uploaded from said at least one ignition interlock device comprises blood alcohol concentration test results, diagnostic information of said at least one ignition interlock device, warnings of hardware failures of said at least one ignition interlock device, speed of vehicle, or information concerning the verification of the operator's identity.

8. The method of claim 1, wherein said secured transactional data comprises at least one of a time data denoting the time at which said data was collected, a date data denoting the date at which said data was collected, an operator data denoting the name of the operator who uploaded said data from said at least one ignition interlock device, and a programming data describing any programming changes to said data uploaded from said at least one ignition interlock device.

9. The method of claim 1, wherein said secure transactional stamp comprises at least one of a time stamp denoting the time at which said data was collected, a date stamp denoting the date at which said data was collected, an operator stamp denoting the name of the operator who uploaded said data from said at least one ignition interlock device, and a programming stamp describing any programming changes to said data uploaded from said at least one ignition interlock device.

10. The method of claim 1, wherein said central database comprises a computer server.

11. The method of claim 1, wherein said authorized third party comprises at least one of a member of court personnel, a member of motor vehicle department personnel, and a member of police department personnel.

12. A method for providing secured and transparent cached ignition interlock data from a breath alcohol ignition interlock device comprising:
    interfacing at least one local computer with at least one ignition interlock device;
    uploading data from said at least one ignition interlock device to said at least one local computer;
    pairing said data with secured transactional data to provide a secure transactional stamp;
    transmitting said data and said paired secure transactional stamp from said at least one local computer to a central database;
    storing said data and said paired secured transactional stamp in said central database;
    reviewing said data and said paired secured transactional stamp for blood alcohol violations and hardware errors;
    logging all actions undertaken in said reviewing step with additional secured transactional data to provide an additional secure transactional stamp;

producing a report comprising said data, said paired transactional stamp and said additional secure transactional stamp; and providing said report to an authorized third party.

13. The method of claim 12, wherein said at least one local computer comprises at least one of a personal digital assistant (PDA) computer, a laptop computer, and a desktop computer.

14. The method of claim 12, wherein said at least one ignition interlock device comprises at least one of a Taguchi cell, an infrared absorption sensing system, a fuel cell, and a transdermal sensing system, and a bodily fluid sensing system configured to sense and quantify the amount of alcohol in a client's breath sample.

15. The method of claim 12, wherein said at least one ignition interlock device comprises at least one of a DRAEGER INTERLOCK® XT device, an Intoxalock device, a LifeSafer Interlock device, a Smart Start's ignition interlock device, an AMS 2000 device, a QuicTest device, and The Determinator device.

16. The method of claim 12, wherein said interface between said central database and said at least one ignition interlock device comprises at least one of a wireless connection and a wired connection.

17. The method of claim 16, wherein said wired connection comprises at least one of a USB connection, an Ethernet connection, a wireless network connection, a DIN connection, a DVI connection, a VGA connection, a DB13W3 connection, and a D-Terminal connection.

18. The method of claim 12, wherein said data uploaded from said at least one ignition interlock device comprises blood alcohol concentration test results, diagnostic information of said at least one ignition interlock device, warnings of hardware failures of said at least one ignition interlock device, speed of vehicle, or information concerning the verification of the operator's identity.

19. The method of claim 12, wherein said secured transactional data comprises at least one of a time data denoting the time at which said data was collected, a date data denoting the date at which said data was collected, an operator data denoting the name of the operator who uploaded said data from said at least one ignition interlock device, and a programming data describing any programming changes to said data uploaded from said at least one ignition interlock device.

20. The method of claim 12, wherein said secure transactional stamp comprises at least one of a time stamp denoting the time at which said data was collected, a date stamp denoting the date at which said data was collected, an operator stamp denoting the name of the operator who uploaded said data from said at least one ignition interlock device, and a programming stamp describing any programming changes to said data uploaded from said at least one ignition interlock device.

21. The method of claim 12, wherein said central database comprises a computer server.

22. The method of claim 12, wherein said authorized third party comprises a member of court personnel, a member of motor vehicle department personnel, and a member of police department personnel in the State of Arizona.

23. A system for providing secured and transparent cached ignition interlock data from a breath alcohol ignition interlock device comprising:

interfacing a central database with at least one ignition interlock device;

uploading data from said at least one ignition interlock device to said central database;

pairing said data with secured transactional data to provide a secure transactional stamp;

storing said data and said paired secure transactional stamp in said central database;

providing an interface for the client of said at least one ignition interlock device to input data;

logging all actions undertaken in said client input step with additional secured transactional data to provide an additional secure transactional stamp;

producing a report with said data, said paired transactional stamp, said client inputted data, and said additional secure transactional stamp; and providing said report to an authorized third party.

24. A method for providing secured and transparent cached ignition interlock data from a breath alcohol ignition interlock device comprising:

interfacing at least one local computer with at least one ignition interlock device;

uploading data from said at least one ignition interlock device to said at least one local computer;

pairing said data with secured transactional data to provide a secure transactional stamp;

transmitting said data and said paired secure transactional stamp from said at least one local computer to a central database;

storing said data and said paired secured transactional stamp in said central database;

reviewing said data and said paired secured transactional stamp for blood alcohol violations and hardware errors;

logging all actions undertaken in said reviewing step with additional secured transactional data to provide an additional secure transactional stamp;

producing a report comprising said data, said paired transactional stamp and said additional secure transactional stamp, wherein said report is admissible under Rule 901(b)(9) of the Federal Rules of Evidence; and providing said report to an authorized third part.

25. A method for providing secured and transparent cached ignition interlock data from a breath alcohol ignition interlock device comprising:

interfacing at least one local computer with at least one ignition interlock device;

uploading data from said at least one ignition interlock device to said at least one local computer;

pairing said data with secured transactional data to provide a secure transactional stamp;

transmitting said data and said paired secure transactional stamp from said at least one local computer to a central database;

storing said data and said paired secured transactional stamp in said central database;

reviewing said data and said paired secured transactional stamp for blood alcohol violations and hardware errors;

logging all actions undertaken in said reviewing step with additional secured transactional data to provide an additional secure transactional stamp;

producing a report comprising said data, said paired transactional stamp and said additional secure transactional stamp, wherein said report is admissible under Rule 902(11) of the Federal Rules of Evidence; and providing said report to an authorized third party.

* * * * *